United States Patent [19]

Fitzgerald

[11] Patent Number: 5,251,644
[45] Date of Patent: Oct. 12, 1993

[54] UPPER EXTREMITY ASSESSMENT SYSTEMS AND METHODS

[75] Inventor: Jacqueline A. Fitzgerald, Shoreview, Minn.

[73] Assignee: Key Functional Assessments, Inc., Minneapolis, Minn.

[21] Appl. No.: 891,287

[22] Filed: May 29, 1992

[51] Int. Cl.$^5$ .............................................. A61B 5/05
[52] U.S. Cl. ...................... 128/782; 128/26; 128/630; 128/898; 108/25; 108/108; 273/265; 273/287
[58] Field of Search ............... 128/630, 774, 782, 26, 128/898; 482/44; 108/25, 26, 108; 273/282.1, 287, 265

[56] References Cited

U.S. PATENT DOCUMENTS

| | | | |
|---|---|---|---|
| 2,794,641 | 6/1957 | Baker et al. | 273/265 |
| 3,129,942 | 4/1964 | Calverley | 273/287 |
| 3,488,053 | 1/1970 | Patel | 128/630 |
| 3,508,753 | 4/1970 | Mackey | 273/287 |
| 3,688,707 | 9/1972 | White | 108/25 |
| 3,814,434 | 6/1974 | Robinson | 273/287 |
| 3,896,718 | 7/1975 | Giambalvo | 108/108 |
| 4,094,255 | 6/1978 | Zaccaria | 108/25 |
| 4,197,855 | 4/1980 | Lewin | 128/782 |
| 4,394,017 | 7/1983 | Maloy | 273/287 |
| 4,779,874 | 10/1988 | Dykstra et al. | 273/287 |
| 4,801,148 | 1/1989 | Lamb | 273/265 |
| 5,121,681 | 6/1992 | Chang | 108/25 |
| 5,154,428 | 10/1992 | Woolhouse | 273/265 |

FOREIGN PATENT DOCUMENTS

| | | | |
|---|---|---|---|
| 3048296 | 7/1982 | Fed. Rep. of Germany | 128/774 |
| 0399012 | 6/1909 | France | 128/630 |

OTHER PUBLICATIONS

R. H. Jebsen et al., "An objective and Standardized Test of Hand Function," *Archives of Physical Medical & Rehabilitation*, 311-19 (Jun. 1969) (Exhibit A).
V. Mathiowetz et al., "Adult Norms For The Nine Hold Peg Test of Finger Dexterity," *The Occupational Therapy Journal of Research*, 5:1 pp. 24-38 (Exhibit B).
V. Mathiowetz et al., "Adult Norms for the Box and Block Test of Manual Dexterity," *The American Journal of Occupational Therapy*, 39:6 pp. 386-391 (Jun. 1985) (Exhibit C).
V. Mathiowetz et al., "Box and Block Test of Manual Dexterity Norms for 6-19 Year Olds," *CJOT*, 52:5, 1 page (Dec. 1985) (Exhibit D).
V. Mathiowetz et al., "The Purdue Pegboard: Norms for 14-19 Year Olds," *The American Journal of Occupational Therapy*, 40:3 pp. 174-175 (Mar. 1986) (Exhibit E).
J. Bear-Lehman et al., "Evaluating the Hand: Issues in Reliability and Validity," *Physical Therapy*, 69:1025-33 and cover page (Dec. 1989) (Exhibit F).

(List continued on next page.)

*Primary Examiner*—Max Hindenburg
*Assistant Examiner*—Jeffrey A. Schmidt
*Attorney, Agent, or Firm*—Merchant, Gould, Smith, Edell, Welter & Schmidt

[57] ABSTRACT

The present invention relates to an upper extremity assessment device usable to test individuals for functional capacity of their upper extremities. The device includes a first support having a first opening. The first support may further include a second opening. A second support with an opening is selectively mounted to the first support, in a perpendicular manner. The openings in the first support and in the second support receive work plates usable in the assessment of the individual. Work plates made from material transparent to visible light are provided to facilitate observation of activity on both sides of each work plate. Structure is provided to selectively mount each work plate in the desired opening. The device itself may be mounted to an assessment rack in a plurality of orientations and a plurality of heights relative to the ground. A variety of assessments may be performed using each work plate.

14 Claims, 5 Drawing Sheets

OTHER PUBLICATIONS

L. A. Jones, "The assessment of hand function: A critical review of techniques," dated Aug., 1990, reprinted from *The Journal of Hand Surgery* 14A pp. 221-228 (1989) (Exhibit G).

V. Mathiowetz, *Dexterity and Hand Function Evaluations*, 6 pages (dated 1988) (Exhibit H).

Table 11-1: "Sampling of tests used in evaluations", 1 page (Exhibit I).

*Preston 1992-92 Catalog*, Cover page and p. 14 (Exhibit J).

*North Coast Medical Inc. Hand Therapy Catalog, 1992*, Cover page and p. 94. (Exhibit K).

*The ITSU Hand Attachments*, 2 pages (Exhibit L).

*BTE Work Simulator*, Pamphlet, Copyright 1990, 5 pages (Exhibit M).

*BTE Bolt Box*, Pamphlet, 1 page (Exhibit N).

*VALPAR VCWS 1 Small Tools (Mechanical)*, Pamphlet, 1 page, Copyright 1986.

*VALPAR VCWS 4 Upper Extremity Range of Motion*, Pamphlet, 1 page, Copyright 1986 (Exhibit P).

*VALPAR VCWS 2 Size Discrimination*, Pamphlet, 1 page, Copyright 1986 (Exhibit Q).

3 Photographs of a product by Key Functional Assessments, Inc., Minneapolis, Minn. (Exhibit R).

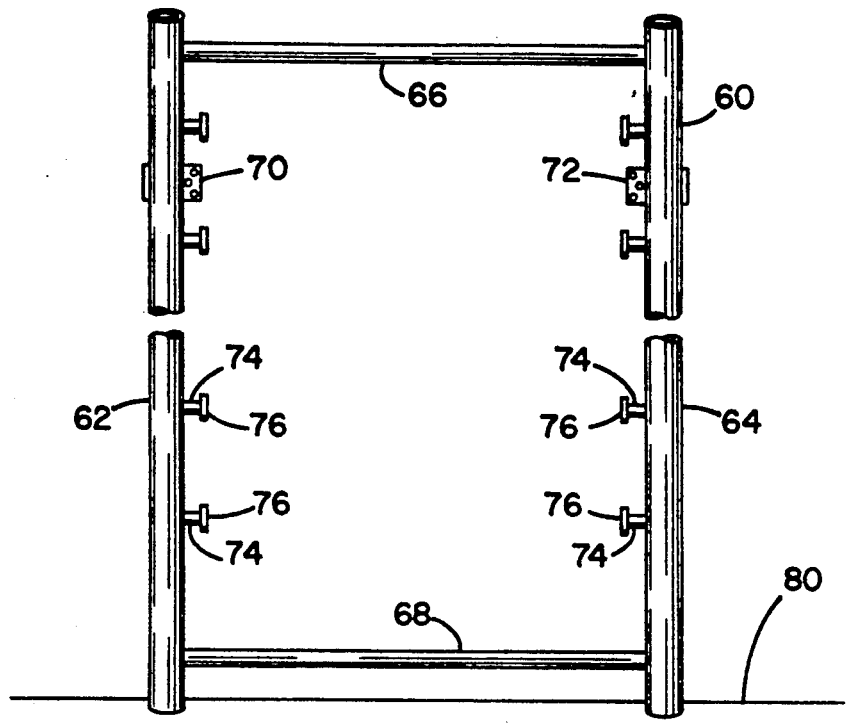
FIG. 3 PRIOR ART
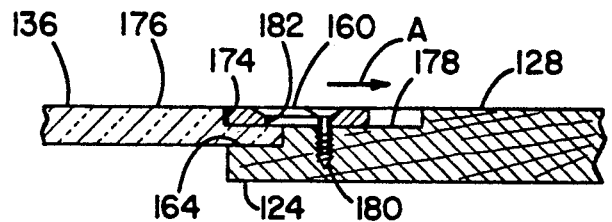
FIG. 8
FIG. 9
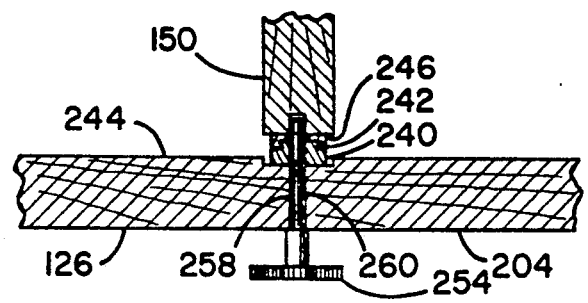

UPPER EXTREMITY ASSESSMENT SYSTEMS AND METHODS

FIELD OF THE INVENTION

The present invention relates to systems and methods for assessing the functional capacity of human patients. More particularly, the present invention relates to devices and methods of using devices for assessing the functional capacity of the upper extremities, including the arms, the hands, and the fingers.

BACKGROUND OF THE INVENTION

The human body can suffer from a variety of injuries and conditions which lessen the functional capacity of the individuals to perform employment related activities and/or leisure activities. When an individual suffers from an injury or a condition which lessens the functional capacity of the person, it is sometimes desireable to measure the extent to which the functional capacity has been lessened. Measuring, or assessing the functional capacity of the individual patient often involves comparing the patient's functional capacity to the functional capacities of others not afflicted with the injury or condition.

With respect to the upper extremities, it is often important to measure the loss of functional capacity for the arms, the hands, and the fingers, due to an injury or a condition. For example, injuries or conditions resulting from employment related activities may require assessment to evaluate and treat the employee, and to evaluate whether the employee can return to work. Repetitive motion disorders, such as Carpal Tunnel Syndrome, have become significant issues in the work place today. Persons afflicted with such disorders may benefit by a functional capacity assessment.

A variety of functional capacity losses are possible for the upper extremities due to an injury or condition which affects the functional capacity of the upper extremities. For example, the injury or condition may affect the person's ability to move the arms, the hands, and/or the fingers. In addition, the injury or condition may have affected the person's ability to use both hands simultaneously. Hand-eye coordination may be affected in some situations. The person's ability to handle small parts and the person's ability to handle tools may be impacted by the injury or condition. Speed and endurance are two aspects of a person's functional capacity that may also be affected by the person's injury or condition.

During an assessment of a patient, the patient carries out a particular test requiring use of at least some portion of the upper extremity. An observer records data from the test, such as whether the tasks requested of the patient are performed properly and how long the tasks took to be completed. In addition, the observer may look for pain behaviors and pain reports. The pain behaviors relate to movements or non-movements of the patient's body which indicate the presence of pain. Pain reports are statements or comments made by the patient during the assessment which reflect pain being felt by the patient.

Typically, the assessment involves an assessment device used by the patient which permits the observer to collect objective data by watching the patient manipulate or handle objects in a predetermined manner. The objective data may then be compared to some normalized results.

With respect to assessment systems and methods, several concerns are important. One concern is establishing tests which are useful in gathering objective data to compare to normalized data. A further concern is that the step of data gathering be fairly easy for the observer making the assessment of the patient. Another concern is that the assessment systems and methods address the problem of the wide variety of injuries and conditions which may require functional capacity assessment. Further, not all functional capacity losses are relevant for each desired activity by the patient. There is a concern that the functional capacity assessment be able to efficiently evaluate the injury or condition in terms of its relationship to the desired activity by the patient.

Functional capacity assessment systems and methods are known for evaluating the functional capacity of a person who has an injury or condition which has lessened the person's functional capacity in some manner. Many of the known upper extremity assessment devices are limited in use. For example, there are known devices that involve a single test for assessing particular functions of the upper extremities. However, these devices are not very useful for the wide variety of different assessments needed. Also, many of the known assessment devices are separate devices which are not useful in a functional capacity assessment system for testing other parts of the body and other functions of the body of the type sometimes used by assessment professionals, such as physical and occupational therapists, chiropractors, exercise physiologists and others.

A need exists in the prior art for assessment systems and methods which address the above concerns, especially providing easy observation, easy standardization, and the versatility to assess a wide variety of injuries and conditions and to address the growing needs of the health care and other industries.

SUMMARY OF THE INVENTION

The present invention relates to an upper extremity assessment device which includes a main support defining an opening through the support. A work plate is positioned at least partially in the opening through the support. Structure is provided for selectively mounting the work plate to the support. Testing structure is associated with the work plate for use in assessing the functional capacity of an upper extremity of a user of the device. Various hardware may be provided, such as bolts, screws, nuts, and electrical components, which the patient is requested to manipulate in a predetermined manner. Various tools, such as screwdrivers, wrenches, and tweezers, may be provided for use by the patient in manipulating the hardware. In some assessments, the patient merely handles the hardware without tools.

Structure is further provided for mounting the support at a predetermined height above the ground. In addition, structure is provided to position the device at one of a plurality of predetermined heights. A rack with a plurality of sets of pegs is preferably provided. Brackets mount the device to the pegs of the rack. Also, mounting structure is provided to permit more than one orientation of the device relative to the ground. For example, a horizontal orientation may be required in one test, while a vertical orientation may be required in a second test. Preferably, a second set of brackets is provided to mount the device in a second orientation relative to the ground.

In a preferred embodiment, the work plate is substantially transparent to visible light to permit viewing of a hand of the patient on one side of the work plate from an opposite side of the work plate. Preferably, a tray for supporting objects used in connection with the work plate is provided for selectively mounting to the support.

To mount the work plate to the support, a lip structure is provided in the opening through the support. A movable clip extends from the support to position a portion of the work plate between the clip and the lip. Structure is provided to lock the clip into place to retain the work plate with the support.

In one preferred embodiment, the support includes a second opening through the support, and a second work plate positioned in the second opening.

In a further preferred embodiment, the device includes a center support which mounts perpendicularly to the first support. Preferably, selective mounting structure is provided to temporarily mount the center support to the main support. In the preferred embodiment, a rail is provided on the center support, and a track for slidably receiving the rail is attached to the main support. A rod is further provided to limit sliding relative movement by inserting the rod perpendicularly through the track and the rail relative to the direction of sliding movement.

The present invention further relates to a method of using an upper extremity assessment device comprising the step of providing a support with an opening therethrough and attaching a first work plate to the support in the opening. The method further comprises performing a first upper extremity function test using the first work plate. Upon completion of the first test, the first work plate is removed from the support. A second work plate is attached to the support in the opening. A second upper extremity function test is performed using the second work plate. The method further preferably comprises changing the orientation of the support relative to the ground prior to performing the second upper extremity function test.

The present invention further relates to a method of using an upper extremity assessment device comprising the step of providing a first support with an opening therethrough, and attaching a first work plate to the first support in the opening. The method further comprises performing a first upper extremity function test using the first work plate. The method comprises providing a second support with an opening therethrough and attaching a second work plate to the second support in the opening. The second support is mounted to the first support. A second upper extremity function test is performed using the second plate. The method further preferably comprises removing the second support from mounting engagement with the first support.

BRIEF DESCRIPTION OF THE DRAWINGS

In the drawings, where like numerals refer to like components throughout the several views:

FIG. 3 is a view of a prior art assessment rack useful in connection with the assessment device shown in FIGS. 1 and 2.

FIG. 8 is an enlarged cross-sectional view of a portion of the assessment device shown in FIGS. 4 and 5, showing the mounting structure for mounting one of the work plates to the main support.

FIG. 9 is an enlarged cross-sectional view of a portion of the assessment device shown in FIGS. 4 and 5, showing the mounting structure for mounting the center support to the main support.

DETAILED DESCRIPTION OF THE PRIOR ART AND THE PREFERRED EMBODIMENTS

Figure 1:
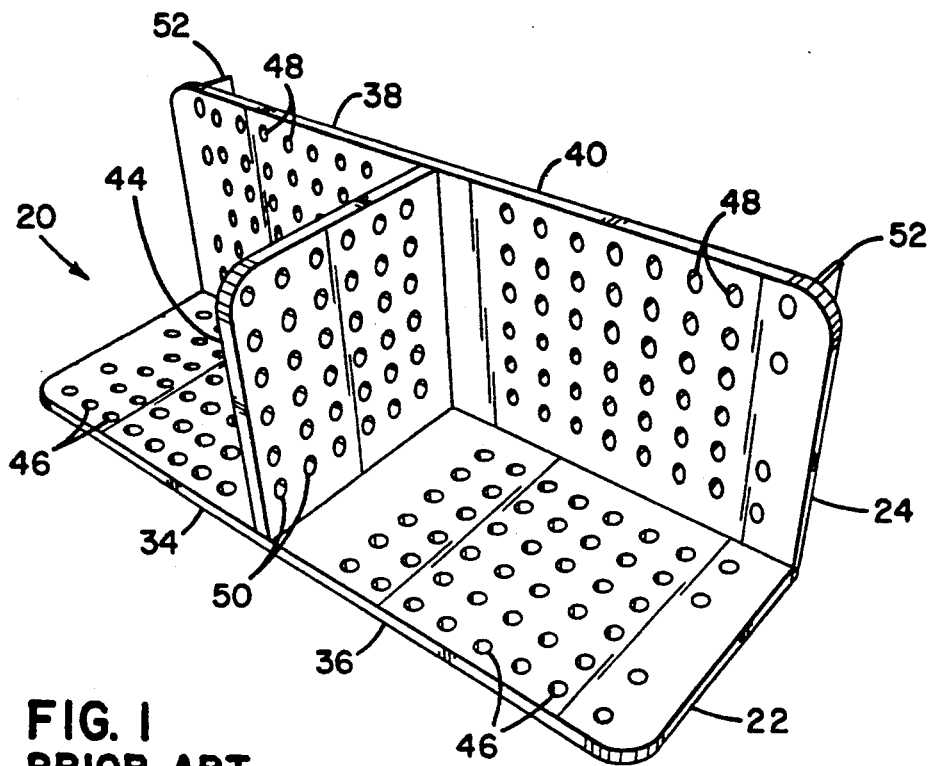
FIG. 1 is a view of a prior art assessment device.
Figure 2:
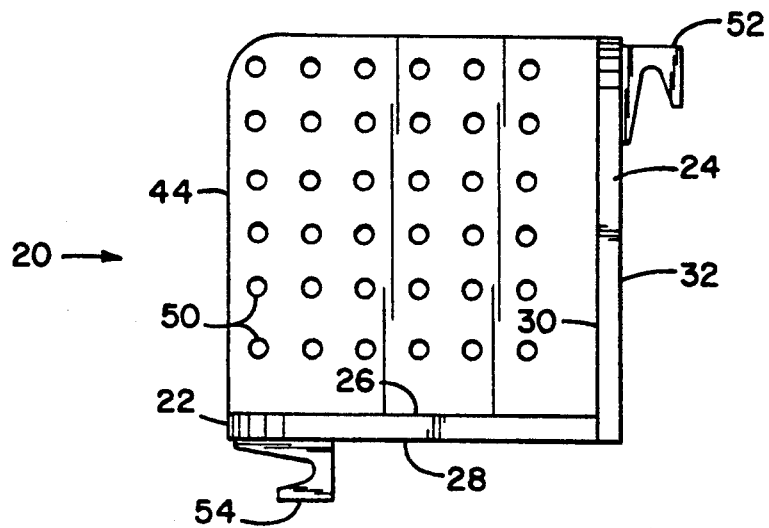
FIG. 2 is an end view of the device shown in FIG. 1.

FIGS. 1-3 relate to features of prior art assessment systems and methods. FIGS. 4-9 illustrate preferred embodiments of the assessment device according to the present invention.

Referring now to FIGS. 1 and 2, a prior art assessment device 20 is shown. Device 20 is useful for assessing the functional capacity of a patient's upper extremities. Device 20 includes a first planar member 22 and a second planar member 24. First planar member 22 includes a first surface 26 and a second surface 28. Second planar member 24 includes a first surface 30 and a second surface 32. As shown in FIG. 1, first planar member 22 is divided into a first half 34 and a second half 36 by a middle planar member 44. Middle planar member 44 also divides second planar member 24 into a first half 38 and a second half 40.

Holes 46 extend through first planar member 22. Holes 48 extend through second planar member 24. Holes 50 extend through middle planar member 44. Holes 46,48,50 are utilized by the patient being assessed. The patient attaches bolts, washers, and nuts to each of the holes, in a predetermined manner requested by the person conducting the assessment. An observer monitors the patient as the patient assembles the bolts, washers, and nuts to at least one of the planar members 22,24,44.

Brackets 52,54 facilitate mounting of device 20 at a height above the ground. Referring now to FIG. 3, an assessment rack 60 is used to position device 20 at the desired height from the ground 80. Rack 60 includes vertical poles 62,64 and horizontal poles 66,68. Wall mounts 70,72 permit positioning of rack 60 at a spaced apart distance from the wall. Vertical poles 62,64 include a plurality of pegs 74 with knobs 76 on each end. Brackets 52 of device 20 mount to one set of pegs 74 of rack 60 at the desired height from the ground. Alternatively, brackets 54 permit mounting of device 20 to rack 60 in a different orientation relative to ground 80. FIG. 2 represents the orientation relative to the vertical of device 20 when brackets 52 are utilized to mount device 20 to rack 60. When brackets 54 are utilized to mount device 20 to rack 60, second planar member 24 is disposed vertically above middle planar member 44, with second planar member 24 having a horizontal orientation relative to ground 80.

Device 20 is an integral device, whereby middle planar member 44 is permanently attached to first and second planar members 22,24. Further each of the planar members 22,24,44 is not transparent to visible light such that activity on one side of one of the planar members is not viewable by an observer on an opposite side of the planar member, except for any light passing through any of the unused holes through the planar member. Also, holes 46,48,50 are uniformly sized, each for slidably receiving a single bolt axially inserted in each hole.

In use, device 20 may be arranged on rack 60 at a predetermined height in a predetermined orientation. The patient whose upper extremities are being assessed would perform a specified task, such as inserting bolts though a predetermined number of holes, then adding a washer and a nut. The observer would collect data and make observations regarding the patient's performance. The data and observations would be utilized to assess the functional capacity of the upper extremities of the patient being tested.

Referring now to FIGS. 4–7, an improved upper extremity device 120 is shown in accordance with principles of the present invention. Device 120 includes a main support 122 including a first member 124 and a second member 126. Preferably, first member 124 and second member 126 are generally planar structures which are rigidly mounted to each other in a perpendicular arrangement to form a generally L-shaped structure.

First member 124 defines a main work surface. First member 124 further includes structure to permit functional testing of a patient's upper extremities. First surface 128 opposes second surface 130 (see FIGS. 6 and 7). Extending from first surface 128 to second surface 130 is a first opening 132. Preferably, a second opening 134 extends from first surface 128 to second surface 130 of first member 124. Opening 132 receives a first work plate 136 which includes testing structure for use in assessing the patient's functional capacity of the upper extremities.

Second opening 134 receives a work plate 138. Work plate 138 includes testing structure for permitting functional capacity assessment of a patient's upper extremities. In accordance with the present invention, the testing structure of work plate 138 can be different from the testing structure of work plate 136, or identical. In the embodiments shown in FIGS. 4–7, the testing structure is different.

Device 120 further includes a center or middle support 150. Middle support 150 also forms a third member 150 which mounts to first member 124 and second member 126 of main support 122 (see FIGS. 5 and 6). Third member 150 includes a first surface 152 and a second surface 154 facing in an opposite direction to first surface 152. Preferably, third member 150 defines a planar structure, with first surface 152 being parallel with surface 154. An opening 156 extends from first surface 152 to second surface 154. Opening 156 receives a third work plate 158. Third work plate 158 is useful in assessing the functional capacity of the patient's upper extremities. Third work plate 158 includes testing structure for use in testing particular aspects of the patient's functional capacity. The testing structure of third work plate 158 is different from the testing structure of first work plate 136 and second work plate 138. It is to be appreciated that the testing structure of third work plate 158 can be identical to one or both of work plates 136,138.

As best shown in FIGS. 4–6 and 8, mounting structure is provided to selectively mount each of the work plates 136,138,158 to the respective openings 132,134,156 of device 120. Clips 160,162 cooperate with lip 164 to mount work plate 136 in opening 132 (see FIG. 4). FIG. 8 shows in greater detail clip 160 and lip 164 of first member 124. Clip 160 is slidable in the direction of arrow A. In the position shown in FIG. 8, clip 160 is in the locked position with respect to retaining first work plate 136 with first member 124. A recess 174 permits flush mounting of clip 160 with a top surface 176 of first work plate 136. Similarly, a recess 178 in first surface 128 of first member 124 permits flush mounting of clip 160 on the rest of first surface 128. By appropriate tightening and loosening of screw 180, clip 160 can be securely maintained in the locked position of FIG. 8, or the unlocked position wherein clip 160 is slidably repositionable toward and away from lip 164. In the preferred embodiment, clip 160 is an oval structure with a center slot 182 formed therein for receiving screw 180. Slot 182 is larger in diameter than a head of screw 180, but smaller than a shaft of screw 180. Screw 180 may include an internal hex head to permit tightening and loosening with a hex wrench.

Clip 162 is configured similarly to clip 160 shown in FIG. 8. Clips 186,188 selectively mount second work plate 138 in opening 134. Lip 190 cooperates with clips 186,188 to position second work plate 138 in second opening 134. The structure of clips 186,188 and lip 190 is identical to the structure shown in FIG. 8 for clip 160 and lip 164. Clips 192,194 cooperate with lip 196 on third member 150 to mount third work plate 158 to third member 150 and opening 156. The structure of clips 192,194 and lip 196 is identical to the structure shown in FIG. 8 for clip 160 and lip 164.

In the preferred embodiments, work plates 136,138,158 are interchangeable with the respective openings 132,134,156. This permits additional testing arrangements depending upon the nature of the injury or condition and the desired assessment. Further, additional work plates may be substituted for work plates 136,138,158. The additional work plates would be mountable in at least one of the openings 132,134,156 through the use of the retaining clips, such as clip 160 shown in FIG. 8.

Figure 6:
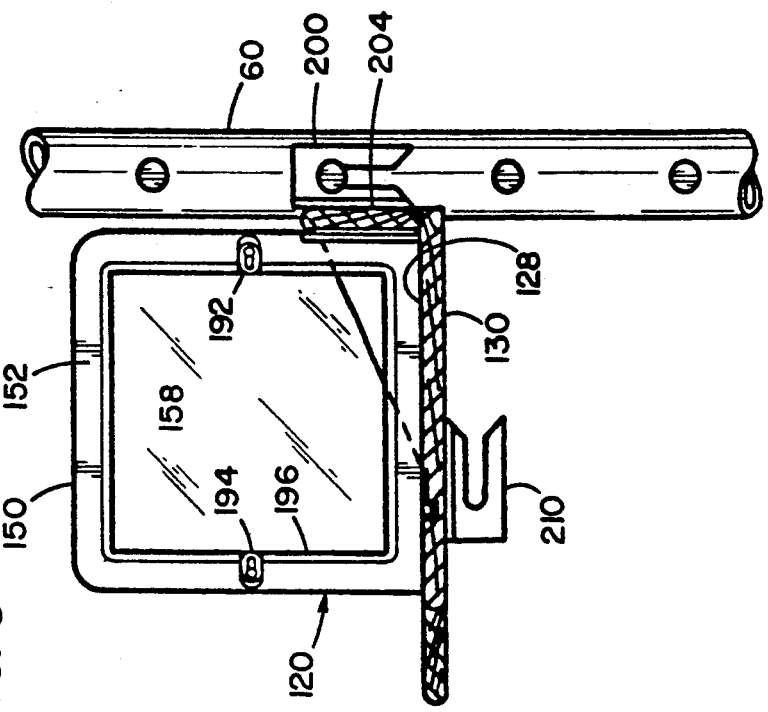
FIG. 6 is a cross-sectional side view of the assessment device shown in FIGS. 4 and 5, showing the assessment device mounted to the assessment rack of FIG. 3 in the first orientation.
Figure 7:
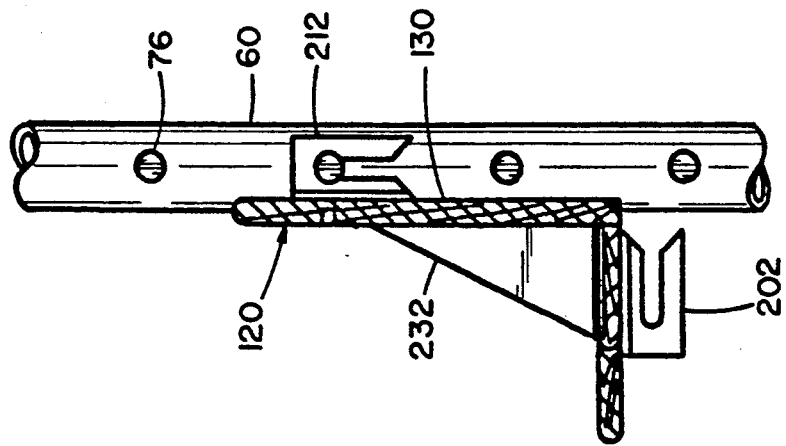
FIG. 7 is a cross-sectional side view of the assessment device shown in FIGS. 4 and 5, showing the assessment device mounted to the assessment rack in a second orientation relative to the ground. In addition, the center support of the assessment device has been removed.

Device 120 is usable with assessment rack 60 shown in FIG. 3. Rack 60 cooperates with structure on device 120 to position device 120 in one of a plurality of predetermined heights with respect to the ground. Preferably, structure is provided on device 120 to permit more than one orientation of device 120 with respect to the ground. FIGS. 6 and 7 illustrate device 120 mounted to rack 60 in two different orientations. Brackets 200,202 mount to second member 126 along a first surface 204 (see FIG. 6). Screws 206 permit attachment of brackets 200,202 to second member 126. Brackets 200,202 permit mounting of device 120 to rack 60 in a first orientation as shown in FIG. 6. Brackets 210,212 permit mounting of device 120 in a second orientation as shown in FIG. 7. Brackets 210,212 mount with screws 214 to second surface 130 of first member 124. Brackets 200,202,210,212 cooperate with pegs 74 and knobs 76 of rack 60 to permit selective mounting of device 120 at a plurality of heights and a plurality of orientations with respect to the ground 80.

Figure 4:
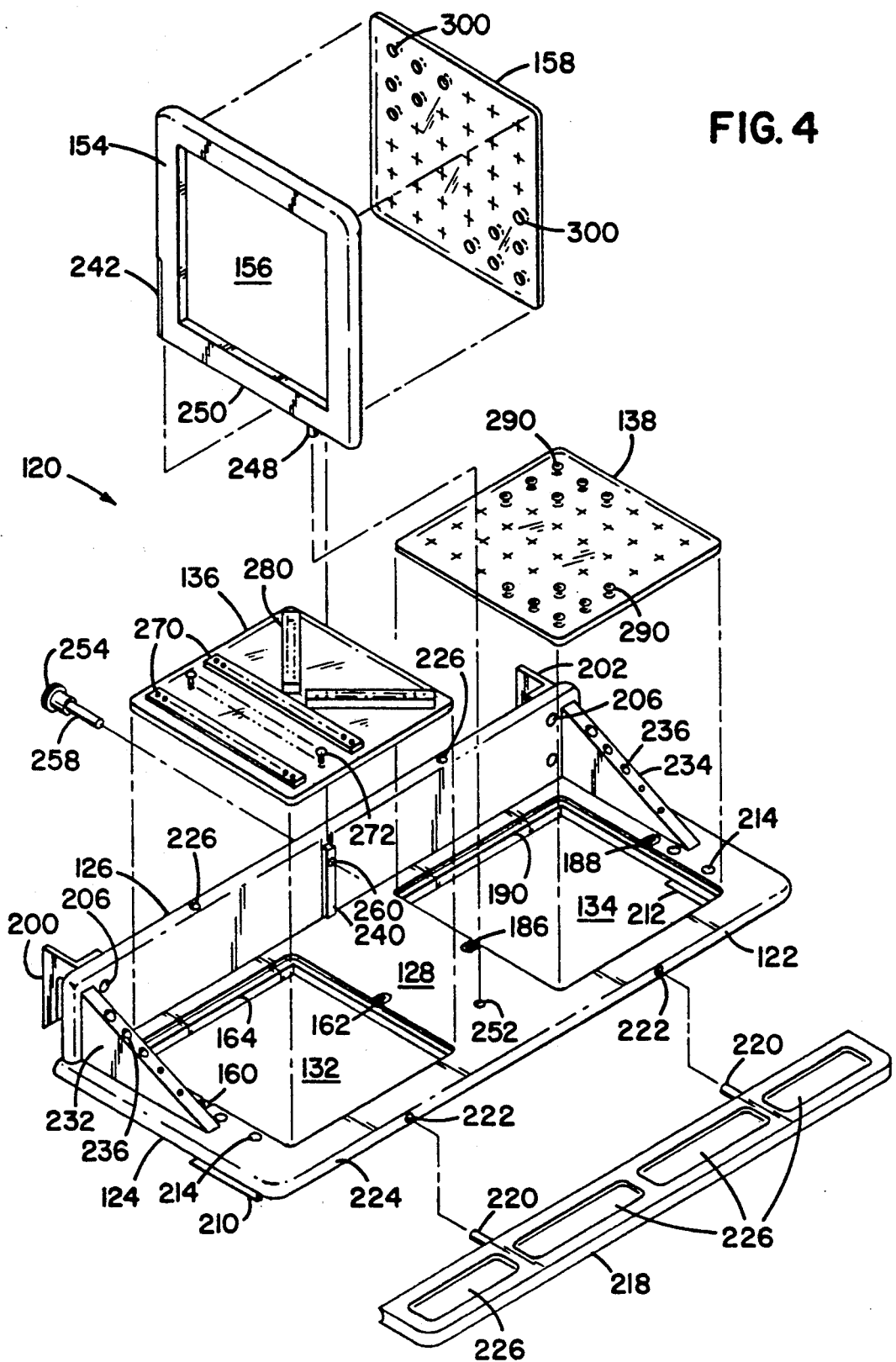
FIG. 4 is an exploded assembly view of an assessment device according the present invention. The assessment device is shown in a first orientation relative to the vertical.
Figure 5:
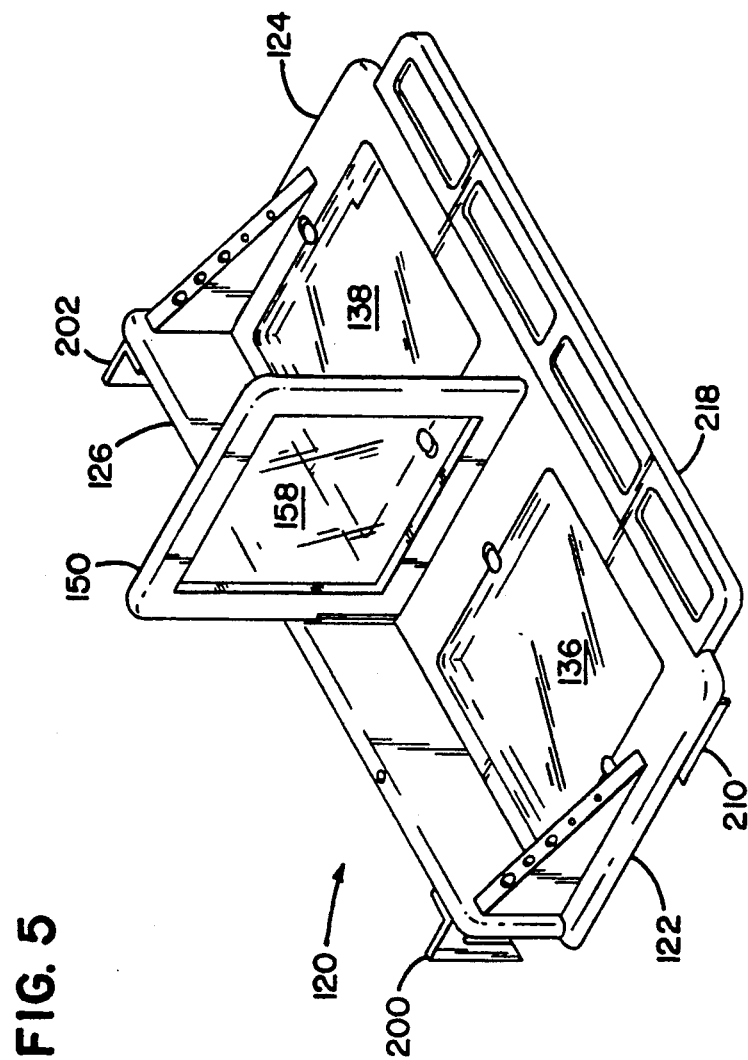
FIG. 5 is an assembled view of the assessment device shown in FIG. 4. Particular features of the device have been eliminated for clarity purposes.

As best shown in FIGS. 4 and 5, device 120 includes a tray 218 for use in holding parts or tools used in connection with one or more of the functional assessment tests. Tray 218 includes pegs 220. Pegs 220 are received by holes 222 in an edge 224 of first member 124. Tray 218 includes recessed portions 226 which help retain parts or tools positioned on tray 218. Preferably, tray 218 includes recessed portions on an opposing side of tray 218 to serve the similar purpose when the orientation of tray 218 is reversed. In use, tray 218 is oriented in a horizontal position with respect to the ground wherein the recessed portions 226 permit holding of tools or parts.

When the orientations of device 120 are switched, such as when device 120 is repositioned between the orientations of FIG. 6 to the orientation of FIG. 7, it is desirable to reposition tray 218 in a more useful position. In the orientation of FIG. 6, the tray is useful in the positions shown in FIGS. 4 and 5. When the device 120 is repositioned to the orientation of FIG. 7, tray 218 is no longer useful in the position shown in FIGS. 4 and 5. Holes 226 are provided to receive pegs 220 to mount tray 218 to an edge 228 of second member 126 when device 120 is in the orientation of FIG. 7.

On opposite ends of device 120 are gussets 232,234. Gussets strengthen the connection between first member 124 and second member 126. Gussets 232,234 include a plurality of holes 236 for use in receiving one or more tools. Holes 236 provide storage locations for tools not used in the particular test by the patient. Holes 236 also provide a convenient structure for temporary storage of tools, such as when the patient is required to use two different tools in a particular sequence. When one tool is not used, it may be stored in one of the holes 236. Similarly, when the tool is needed, the patient removes the tool from hole 236 and places the unused tool in one of the unused holes 236.

In the preferred embodiment, third member 150 is selectively mountable to main support 122. FIGS. 5 and 6 illustrate third member 150 temporarily mounted to main support 122. This position is referred to as the sagittal position of third member 150. In some functional capacity assessments, this position is desirable. In the sagittal position, the patient typically accesses both sides of third work plate 158, one with each hand with the work plate extending vertically in front of the patient.

A selective mounting of third member 150 is useful. In some functional capacity assessments, the sagittal position is not needed. Further, third member 150 in the sagittal position may interfere with other functional capacity assessments being performed with either or both of the first and second work plates 136,138, in any orientation of device 120. Also, storage and transport of device 120 may be easier since third member 150 is removable.

Selective mounting of third member 150 with main support 122 is achieved with a rail 240 and a track 242. Preferably, rail 240 extends from second surface 244 of second member 126. This structure is shown in greater detail in FIG. 9. Track 242 preferably extends from third member 150 along a first edge 246 of third member 150. Rail 240 is preferably T-shaped and fits within a channel on track 242. Rail 240 and track 242 are configured to slidably move relative to each other in a direction parallel to edge 246 of third member 150 and parallel to surface 244 of second member 126.

To further assist in temporarily mounting third member 150 to main support 122, a peg 248 extends from a second edge 250 of third member 150. Peg 248 is received by a hole 252 in first surface 128 of first member 124. Peg 248 limits rotational type movement of third member 150 relative to second member 126 about an axis located adjacent to the rail 240 and track 242 interface and parallel to the direction of sliding relative movement.

To prevent rail 240 and track 242 from sliding relative to one another once third member 150 is placed in its desired position, a lock 254 with a post 258 is provided. Post 258 is slidably inserted through a hole 260 through second member 126 and also through holes provided in rail 240 and track 242 aligned with hole 260. Post 258 prevents relative sliding movement between rail 240 and track 242 until such sliding movement is desired to remove third member 150 from mounting connection to main support 122. Once removal is desired, post 258 is removed and then third member 150 can be slidably removed.

Work plate 136 includes structure for testing particular aspects of the patient's functional capacity. In particular, work plate 136 has testing means including wire regions 270 and pegs 272. Wire regions 270 include holes for receiving screws (not shown) which are designed to receive a plurality of sets of U-clips attached to ends of pieces of wire (not shown). The U-clips and wires may be supplied with device 120, or the end user (person performing assessment) can supply them. The patient may mount the U-clips to the screws by tightening down the screws, and also wrapping the attached wires in a predetermined pattern around pegs 272. Alternatively, other structure can be supplied to or by the end user as desired to cooperate with the screw holes in wire regions 270 and the pegs 272 during an assessment.

Work plate 136 also may include other testing means in addition to or alternative to wire regions 270 and pegs 272. The testing means of work plate 136 includes parts region 280 on first work plate 136. Parts region 280 include small holes. In one preferred assessment, holes 282 are provided for receiving protruding wires from such electrical components as capacitors and resistors (not shown). These may be positioned in the holes in parts region 280 by the patient during assessment. Tweezers may be used by the patient in connection with handling the small electrical components, as part of the assessment. Alternatively or in addition to, a variety of other objects for cooperating with holes 282 during an assessment can be supplied.

Second work plate 138 also includes testing means including a plurality of holes with threads 290. The patient screws and/or unscrews various parts into the threaded holes during an assessment. The threaded parts may be identical or may vary in size and shape. If the parts vary in size and shape, they may also vary in the nature of the tools which they are used in connection with. For example, work plate 138 includes six rows and six columns of threaded holes 290. The patient may be asked to assemble six different rows of hardware. For example, the first row of hardware may includes screws with a large hexagonal head. The second row may include screws with small hexagonal heads. The third row may includes slot headed screws. The fourth column may include Phillips' head screws. The fifth column may include a threaded bolt having a hex head, a threaded hex nut and a washer. The sixth row may include a threaded bolt with a wing nut threadably mounted to the bolt. The order can be specified as desired by the observer making the assessment.

The various tools used in connection with work plate 138 can vary. In particular, screw drivers which are of various sizes may be used, and also variations according to Phillips' head or flat head may be used. L-shaped hex head wrenches of various sizes may be used in connection with the hardware. A nut driver, shaped similarly to a screw driver, but with a hex internal head may be used in connection with some of the hardware. Other tools may be used depending upon the nature of the injury or the condition and the desired assessment. Of course, the tools may vary as the size and shape of the desired hardware varies.

Work plate 158 has testing means including a plurality of holes 300. Holes 300 are sized to receive bolts (not shown). During an assessment, the patient may insert a plurality of bolts through holes 300 and attach a washer (not shown) and nut (not shown) to each bolt. The nuts and bolts may be assembled by hand or by using tools to assist the patient. Various sizes of bolts, nuts and washers may be used.

In use, device 120 is positioned at a desired height and a desired orientation with respect to the ground. The desired work plate 136,138,158 is also positioned in the desired opening 132,134,156. Following arrangement of the desired work plate in the desired location on device 120 at the desired height and the desired orientation, the patient performs the desired assessment. The observer records data such as time and number of repetitions completed. The observer also notices movements or non-movements by the patient and verbal comments made by the patient. Pulse rates may be measured. Normalization of the objective data, by comparing the observed data to data from subjects not afflicted with the injury or condition, is desirable for some functional assessments of the patient.

Once the first assessment is completed by the patient, the patient may be directed to do a second assessment. The second assessment can take place with respect to the same opening where the first assessment was performed. In that case, the previously used work plate may be removed and a new work plate inserted in the opening vacated by the first work plate.

Alternatively, a second work plate positioned in a different opening may be used and a second test performed with respect to the second work plate. The second plate may be added before or after the patient performs the first test.

Alternatively, a second test can be done in connection with the first work plate left in the same opening. Such test might occur in the same or a different orientation than during the first test.

A plurality of assessments may be performed using some or all of work plates 136,138,158, or other work plates, wherein the work plates are positioned at one or more heights and at one or more orientations relative to the ground.

Third member 150, if not involved in the particular assessment being performed, can be either removed or attached to main support 122 during performance of the particular assessments.

Some assessments are desireable wherein device 120 is positioned in the orientation of FIGS. 4-6, and third member 150 is not present. It may be easier for the patient to access the first or second work plate 130,132. Also, in this arrangement, device 120 may form a table top for supporting a separate testing device, such as a keyboard of a computer, or a typewriter to test the patient's ability to type.

Various combinations are possible with respect to the work plates and the various positions of the work plates with the various positions possible for device 120. It is to be appreciated that work plates other than work plates 136,138,158 and the tests associated with each work plate, including the hardware and tools used to perform the tests, can be varied in accordance with the present invention.

In the preferred embodiments, work plates 136,138,158 are sufficiently transparent that an observer on one side of the work plate can at least substantially view the hand of the patient positioned on an opposite side of the work plate. This permits better information gathering by the observer during assessment. Clear plexiglass works adequately. First, second, and third members of device 120 can be made from any material. Wood works adequately in the preferred embodiment.

Device 120 permits a variety of assessments using device 120 to address the variety of injuries and conditions affecting the patient. Further, the assessments are sufficiently variable and yet easily standardizable to permit meaningful usage in assessments for particular injuries and conditions as they relate to the desired activity by the patient. Since device 120 is movable in a variety of positions and the work plates are movable with respect to device 120, a more versatile device 120 results. Further, device 120 is useable in connection with rack 60. Rack 60 may be used as part of a functional capacity system used by assessment professionals for assessing other functional capacities of the body, some unrelated to the upper extremities.

The invention is not to be construed as to be limited to the specific embodiments shown in the drawings, but is to be limited only by the broad general meanings of the following claims.

What is claimed is:

1. An upper extremity assessment device comprising:
a first support having an opening therethrough, the first support defining a first plane;
a work plate positioned at least partially in the opening through the first support;
testing means, associated with the work plate, for assessing the functional capacity of an upper extremity of a user of the device;
means for selectively mounting the work plate to the first support;
a second support extending from the first support and defining a second plane perpendicular to the first plane;
a third support defining a third plane;
testing means, associated with the third support, for assessing the functional capacity of an upper extremity of the user of the device; and
means for selectively mounting the third support to at least one of the first support and the second support such that the third plane defined by the third support is perpendicular to the first plane defined by the first support and perpendicular to the second plane defined by the second support.

2. The device of claim 1, further comprising:
a rack; and
bracket means for mounting the first support to the rack at a predetermined height above the ground.

3. The device of claim 1, wherein the work plate is substantially transparent to visible light to permit viewing of a hand of the user of the device on one side of the work plate from an opposing side of the work plate.

4. The device of claim 1, further comprising:
a tray for supporting objects used with the work plate; and
means for selectively mounting the tray to the first support.

5. The device of claim 1, wherein the means for selectively mounting the work plate to the first support includes:
a retaining lip extending from the first support;
a moveable clip extending from the first support;
means for locking the clip in a locked position relative to the first support, the clip in the locked position being spaced apart from the lip to define a gap for receiving a portion of the work plate; and
the work plate being mounted to the first support when a portion of the work plate is positioned in the gap between the clip and lip and the clip is in the locked position.

6. The device of claim 1, wherein the first support further has a second opening therethrough, the device further comprising a second work plate positioned at least partially in the second opening, testing means, associated with the second work plate, for assessing the functional capacity of an upper extremity of the user of the device, and means for selectively mounting the second work plate to the first support.

7. An upper extremity assessment device comprising:
a first support having a first planar surface and a second planar surface facing in an opposite direction to the first planar surface, the first support further having an opening therethrough;
a work plate positioned at least partially in the opening through the first support;
testing means, associated with the work plate, for assessing the functional capacity of an upper extremity of a user of the device;
means for selectively mounting the work plate to the first support; and
means for mounting the first support at one of a plurality of predetermined heights above the ground wherein the first and second planar surfaces are in a first orientation relative to the ground, said means for mounting the first support including rack means including a plurality of sets of pegs and cooperating brackets for mounting the first support at one of the plurality of predetermined heights above the ground.

8. The device of claim 7, wherein the device further comprises:
a second support having a first planar surface and a second planar surface facing in an opposite direction to the first planar surface, the second support further having an opening therethrough;
a second work plate positioned at least partially in the opening through the second support;
testing means, associated with the second work plate, for assessing the functional capacity of an upper extremity of the user of the device;
means for selectively mounting the second work plate to the second support; and
means for selectively mounting the second support to the first support such that the first planar surface of the first support is perpendicular to the first planar surface of the second support.

9. An upper extremity assessment device comprising:
a first member including a first work surface generally defining a first plane;
a second member including a second work surface generally defining a second plane, and testing means, associated with the second member, for assessing the functional capacity of an upper extremity of a user of the device;
means for selectively mounting the first member to the second member such that the first plane defined by the first work surface is generally perpendicular to the second plane defined by the second work surface, wherein the means for selectively mounting includes:
a guide rail extending from the first member;
a guide track extending from the second member, the guide rail slidably received by the guide track to mount the first member to the second member;
means for selectively mounting the second work plate to the second support; and
means for selectively mounting the second support to the first support such that the first planar surface of the first support is perpendicular to the first planar surface of the second support.

10. The device of claim 9, wherein the means for selectively mounting further includes a rod, a first opening passing through the guide rail, and a second opening passing through the guide track, the rod being inserted through the first opening through the guide rail and the second opening through the guide track in a direction perpendicular to the direction of sliding relative movement between the guide rail and the guide track during mounting of the first member to the second member to limit sliding relative movement.

11. The device of claim 9, further comprising means for mounting at least one of the first and second members at a predetermined height above the ground.

12. The device of claim 9, further comprising testing means, associated with the first member, for assessing the functional capacity of an upper extremity of the user of the device.

13. A method of using an upper extremity assessment device comprising the steps of:
providing a first support with an opening therethrough;
attaching a first work plate to the first support in the opening;
performing a first upper extremity function test using the first work plate attached to the first support;
providing a second support with an opening therethrough;
attaching a second work plate to the second support in the opening;
mounting the second support to the first support;
performing a second upper extremity function test using the second plate attached to the first support.

14. The method of claim 13, further comprising the step of removing the second support from mounting engagement with the first support.

* * * * *

UNITED STATES PATENT AND TRADEMARK OFFICE
CERTIFICATE OF CORRECTION

PATENT NO. : 5,251,644

DATED : October 12, 1993

INVENTOR(S) : Jacqueline A. Fitzgerald

It is certified that error appears in the above-identified patent and that said Letters Patent is hereby corrected as shown below:

Claim 9, Column 12, lines 23-28, delete "means for selectively mounting the second work plate to the second support; and means for selectively mounting the second support to the first support such that the first planar surface of the first support is perpendicular to the first planar surface of the second support."

after the word "member;"

Claim 9, Column 12, line 22, after the second occurrence of "member", delete ";" and insert "."

Signed and Sealed this

Nineteenth Day of April, 1994

*Attest:*

BRUCE LEHMAN

*Attesting Officer*     *Commissioner of Patents and Trademarks*